United States Patent [19]
Reynolds et al.

[11] Patent Number: 5,423,603
[45] Date of Patent: Jun. 13, 1995

[54] HIGH/LOW PROFILE ROCKER

[75] Inventors: Cedric S. Reynolds, Greensboro, N.C.; Albert B. Reynolds, Jr., Memphis, Tenn.; Frank Jolly, Arcata; Kent Jolly, Sacramento, both of Calif.; Michael C. Liebal, Greensboro, N.C.

[73] Assignee: Stovall Life Science, Inc., Greensboro, N.C.

[21] Appl. No.: 219,928

[22] Filed: Mar. 30, 1994

[51] Int. Cl.⁶ ............................................. B01F 11/00
[52] U.S. Cl. ..................... 366/208; 366/601
[58] Field of Search ............. 366/208, 209, 210, 211, 366/215, 216, 239, 218, 237, 238, 605, 166, 14, 219, 331, 601, 239; 422/99; 99/277.1, 277.2

[56] References Cited
U.S. PATENT DOCUMENTS

| | | | |
|---|---|---|---|
| 2,834,585 | 5/1958 | Oharenko | 366/209 |
| 3,788,611 | 1/1974 | Barbini | 366/208 |
| 4,893,938 | 1/1990 | Anderson | 366/208 |

Primary Examiner—Robert W. Jenkins

[57] ABSTRACT

A low profile platform mixer has a variable number of platforms. The degree of pivot or tilt the platforms undergo can be changed as can the motor speed, depending on the particular laboratory solutions which are to be stirred or agitated. The mixer is made from stainless steel and is suitable for autoclaving to insure cleanliness and sanitation. A stainless steel base rigidly supports a pair of stanchions to which platforms are pivotally connected. The motor and motor controls are also mounted on the base and the motor extends above the height of the first or lowest platform for use in limited space environments.

19 Claims, 4 Drawing Sheets

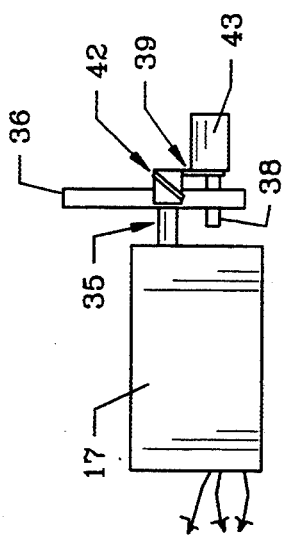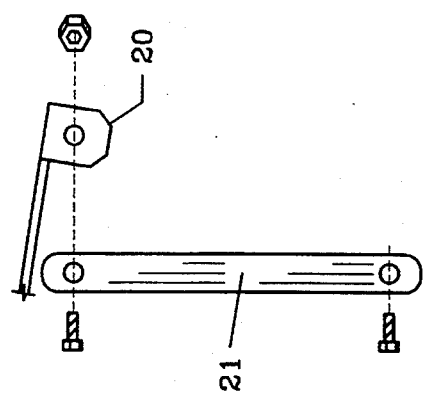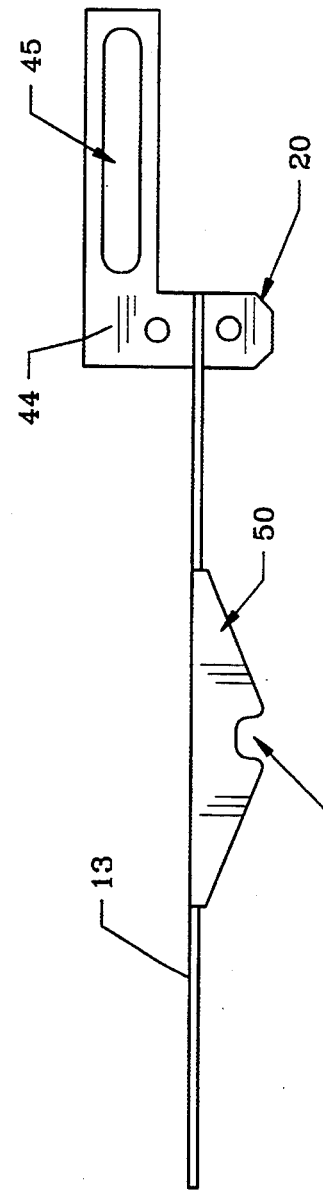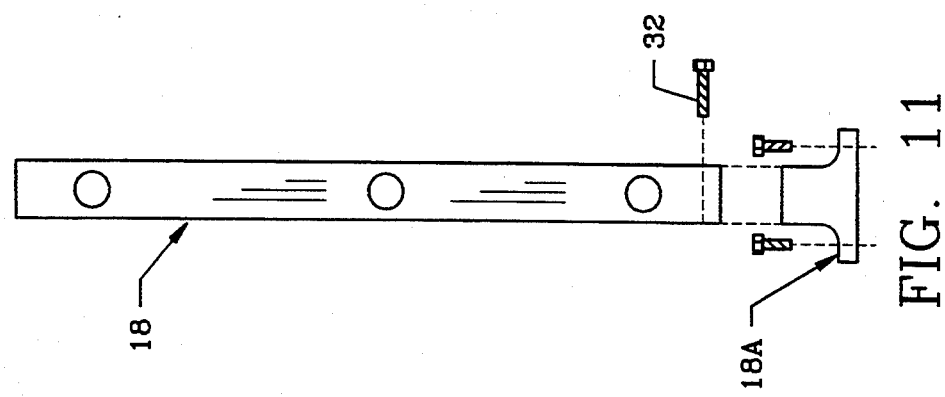

5,423,603

HIGH/LOW PROFILE ROCKER

BACKGROUND OF THE INVENTION

1. Field Of The Invention

The invention herein pertains to a mixing device and particularly to a laboratory mixer having one or more platforms which pivot in a precise controlled manner.

2. Description Of The Prior Art And Objectives Of The Invention

In recent years the scientific community has demanded laboratory equipment for precise stirring, blending, agitating and mixing for sensitive solutions. Cell cultures, staining gels, phage elution, hybridizations and the like often require blending of one or more materials in a precise, closely regulated manner. Certain of these solutions and materials can be damaged if the agitation is too severe. Certain of such solutions and experimental materials are extremely sensitive to environmental pollution and damage to them can easily occur if contaminated or polluting laboratory equipment is used in or near the same. The degree of cleanliness required in most laboratory work is generally greater than it was just twenty years ago and laboratory equipment must perform to more exacting standards, not required in the recent past.

Thus, with the disadvantages and problems associated with prior laboratory mixing devices, the present invention was conceived and one of its objectives is to provide a low profile platform mixer which can be used under a variety of conditions and environments without fear of contamination or pollution to the experimental materials.

Another objective of the present invention is to provide a low profile mixer in which one or more platforms can be used when placed in incubators or the like having relatively low inside heights.

It is still another objective of the present invention to provide a platform mixer which is formed of stainless steel and which can be easily and quickly disassembled and sterilized in an autoclave for complete removal of all debris, contaminants and bacteria.

It is yet another objective of the present invention to provide a platform mixer in which the degree of tilt and speed of the platform can be easily adjusted.

It is yet still another objective of the present invention to provide a platform mixer in which the motor housing can be easily removed for cleaning and sterilizing purposes.

Another objective of the present invention is to provide a platform mixer in which several additional platforms can be added as required.

It is also another objective of the present invention to provide a platform mixer which includes a cam having an adjustable cam follower to regulate the platform tilt in a speedy and simple manner.

Other objective and advantages of the present invention become apparent to those skilled in the art as a more detailed description is set forth below.

SUMMARY OF THE INVENTION

The aforesaid and other objectives of the invention are realized by a low profile platform mixer for use in stirring or blending laboratory solutions and materials formed of stainless steel which includes a lower or first platform which is pivotally joined between opposing stanchions mounted on a rigid planar base. Stanchions of varying lengths for the desired number of platforms are used and are readily exchangable. A removable motor housing is positioned on the base containing a sealed motor and which drives the platform through a cam arrangement. The sealed motor is powered by a 110 v AC or 220 v AC source and turns at a low rpm and is adjustable by a control knob located on the front of the motor housing. A cam has an adjustable cam follower for changing the degree of tilt or rotation of the platform as desired. One or more additional platforms in direct vertical alignment with the first platform can be rapidly and conveniently installed for blending or stirring a larger number of containers holding sensitive solutions and a thin, friction producing surface is secured to the top of each platform to insure stability of the containers during mixing. Each platform has a depending tab for connection through a drive link with adjacent platforms whereby each platform pivots or tilts to the same degree simultaneously with the one above and below. Longer or shorter stanchions respectively can be used if additional platforms are added or removed from the mixer base.

BRIEF DESCRIPTION OF THE DRAWINGS

FIG. 9 demonstrates a side view of the motor removed from the housing with the cam attached to the motor shaft;

FIG. 10 pictures a front view of the bottom or first platform with the cam connector joined thereto but with the platform removed from the base;

FIG. 11 demonstrates a stanchion for a three platform mixer exploded from the stanchion base; and FIG. 12 illustrates in exploded fashion a platform drive link removed from a partially shown platform.

DESCRIPTION OF THE PREFERRED EMBODIMENT

Figure 4:
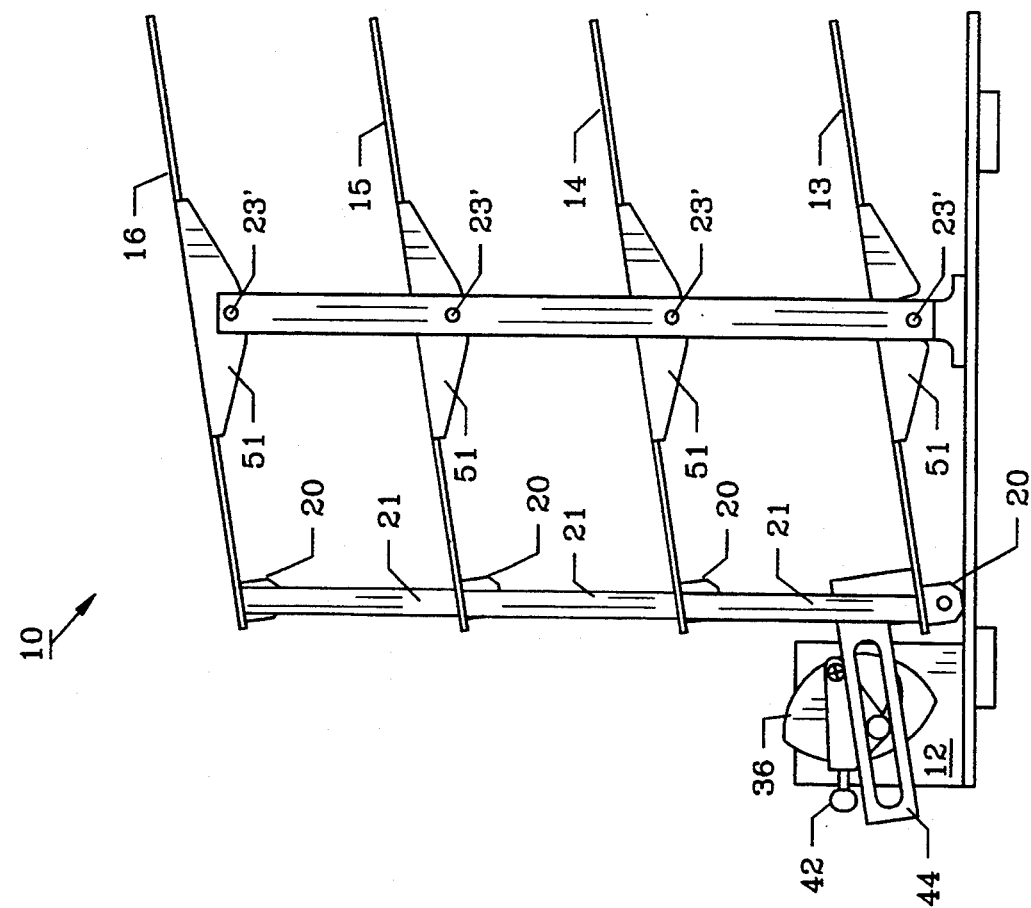
FIG. 4 depicts a rear view with platforms tilted.
Figure 5:
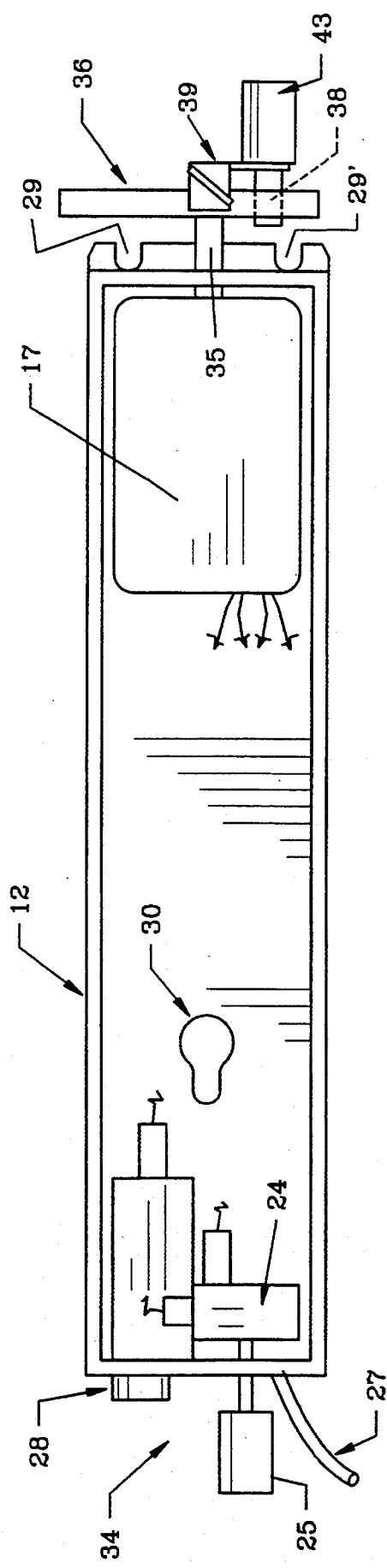
FIG. 5 features an enlarged top view of the motor housing with the top cover removed to expose the motor therein.
Figure 7:
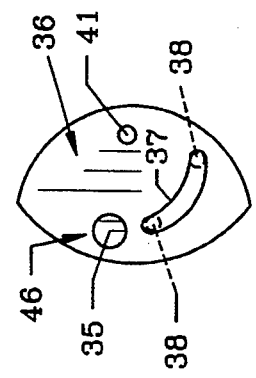
FIG. 7 shows a front view of the cam with the cam follower pivotally attached thereto.
Figure 6:
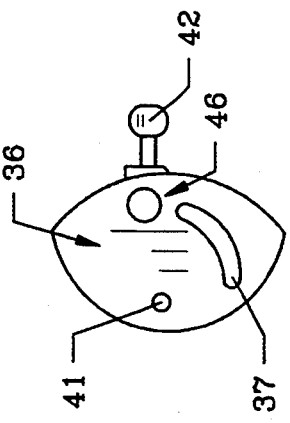
FIG. 6 pictures a rear elevational view of the elliptically-shaped cam removed from the motor.
Figure 8:
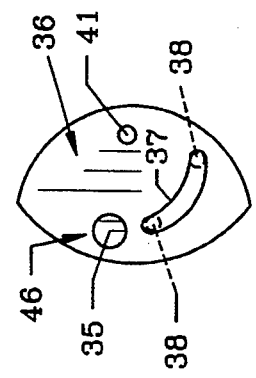
FIG. 8 depicts a front view of the cam but with the cam follower removed to better expose the arcuate slot therein.

The preferred embodiment of the invention is shown in FIGS. 1–12 whereby a platform mixer includes four vertically aligned platforms mounted between opposing stanchions on a planar base. The platforms are connected by a somewhat elliptically shaped cam as shown in FIGS. 6–8 which has an adjustable follower. The motor is a low rpm AC electric motor. The preferred platform mixer is formed substantially of stainless steel and can be autoclaved as necessary for sterilization purposes. The mixer includes a motor control with a knob to vary the rpms and an adjustable cam follower allows the degree of tilt of the platform to be precisely and evenly adjusted. The cam is formed from a hard, durable plastic and includes an arcuate slot which receives a cam follower stud. A thumb screw positioned in the cam follower along the edge of the cam will allow the cam follower to be moved to an exact position for the precise platform tilt needed.

The preferred size of the stainless steel platforms is twelve inches by twelve inches by one-sixteenth inch thick and the base is slightly larger, approximately thirteen and one-half by fifteen by one-eighth inches in thickness. The platforms are connected one to another by stainless steel link members positioned therebetween as seen in FIG. 12. Triangular shaped braces beneath the platforms supply extra rigidity and define axle apertures. The lowermost platform has a slot in the front triangular shaped brace rather than an aperture for safety purposes. A thin rubber or other friction producing surface is affixed to the top of each of the platforms to maintain containers, dishes or the like thereon during platform movement. The friction producing surfaces are releasably attached and the motor housing can be easily removed from the base to facilitate autoclaving for sterilization purposes.

DETAILED DESCRIPTION OF THE DRAWINGS

AND OPERATION OF THE INVENTION

Figure 1:
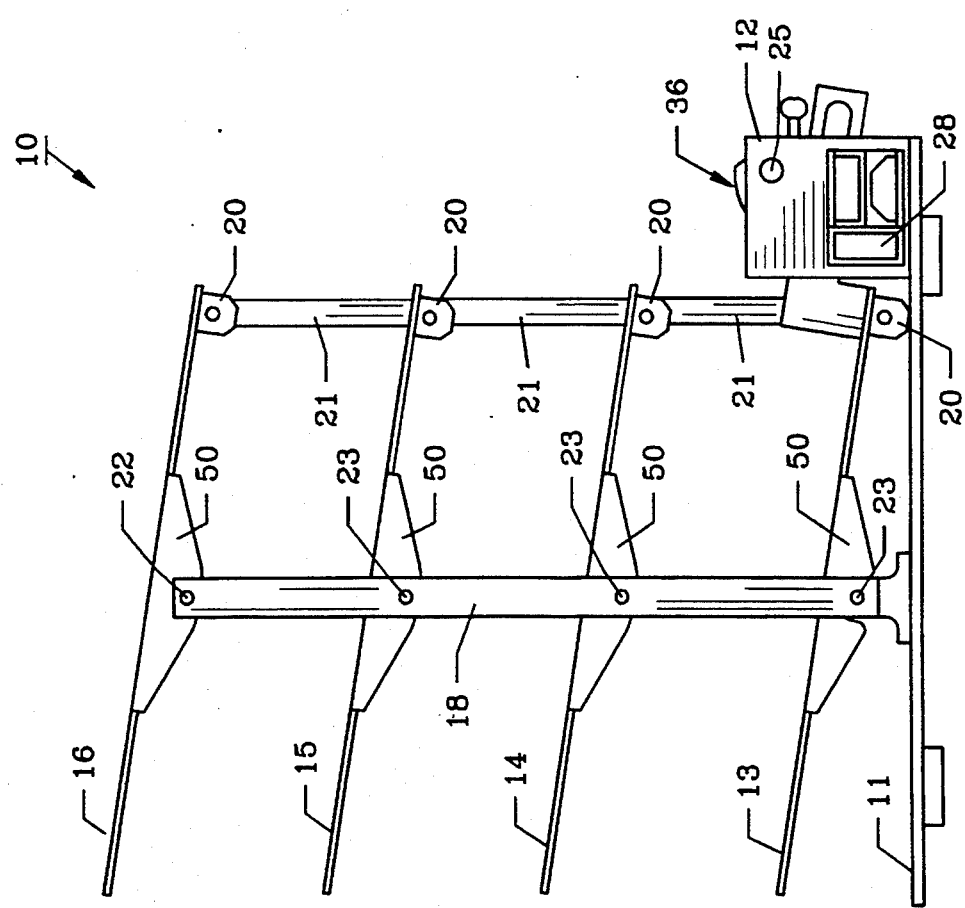
FIG. 1 shows a front elevational view of the mixer as described herein with the platforms tilted.

For a more complete understanding of the invention and its operation, turning now to the drawings, FIG. 1 illustrates low profile platform mixer 10 having a rectangular planar base 11 and an electric motor housing 12 mounted on base 11. Positioned directly above base 11 are a plurality of pivotal square platforms 13-16. Platforms 13-16 are all of the same dimensions (twelve inches by twelve inches) and are formed from a high quality stainless steel as is motor housing 12 and base 11. AC motor housing 12 contains a low rpm 24 v DC electric motor 17 as seen schematically in FIG. 5 with housing cover (not shown) removed. Platform mixer 10 is useful in various chemical, biological and other categories of scientific research, development and testing work of which the utmost in cleanliness, sanitation and mixing precision is mandatory.

While four platforms 13-16 are shown in FIGS. 1, 2, 3 and 4, more or less platforms may be useful under particular circumstances. Thus, front stanchion 18 and rear stanchion 19 can be removed and replaced with longer or shorter stanchions designed respectively for more or less platforms. Stanchion 18 as shown in FIG. 11 is mounted on front stanchion base 18A. As shown in FIG. 11, base 18A comprises a rigid plastic member which is bolted to mixer base 11 and stanchion 18 comprises a square stainless steel tube which in turn is secured to stanchion base 18A by bolt 32. Shorter or longer stanchions can be fabricated and the user may desire one platform or more depending on the number of containers or petri dishes to be agitated simultaneously. As further shown in FIG. 1, platforms 13-16 have a downwardly depending edge tab 20 shown enlarged in FIG. 12 to which drive link 21 is attached. In FIG. 1 three such drive links 21 are shown for connecting platforms 13-16 together.

Figure 2:
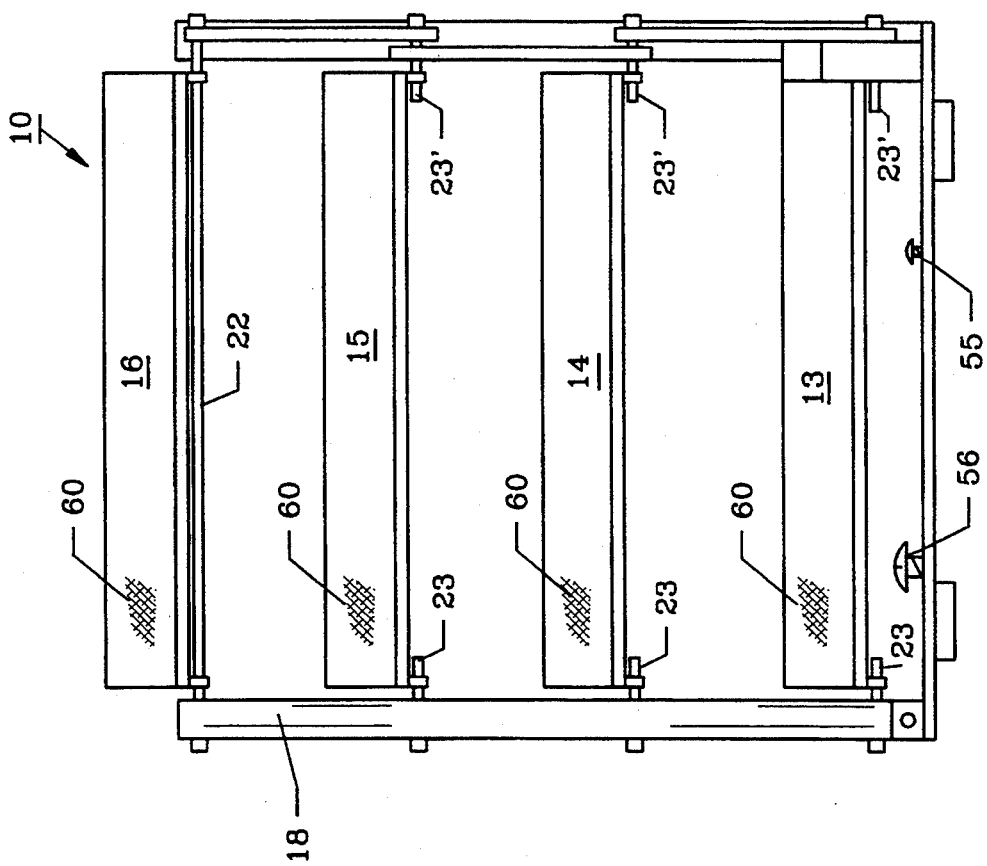
FIG. 2 demonstrates a right side elevational view of the mixer as shown in FIG. 1 with the motor housing removed.

Each platform 13-16 rotates about axles or pivot points which are vertically aligned along stanchions 18 and 19. As shown in FIG. 2, platform 16 is joined to stanchions 18 and 19 by axle rod 22 whereas platforms 13-15 are pivotally joined to stanchions 18 and 19 by axle studs 23, 23'. Axle studs 23, 23' are short to provide more space between platforms 13 and 14, 14 and 15, thereby allowing taller containers or dishes to be placed between platforms 13 and 14 and 14 and 15 during mixing operations. As further seen in FIG. 1, motor housing 12 extends above lower platform 13 to provide a more compact configuration for situations involving relatively little space, for example when mixer 10 utilizes only one platform and is used within a small oven or other small volume container. Friction producing top surface 60 as seen in FIG. 2 may be releasably affixed by screws (not shown) or other means to assist the stability of containers placed on platforms 13-16. Surface 60 may consist of a fabric, rubber film or the like.

Figure 3:
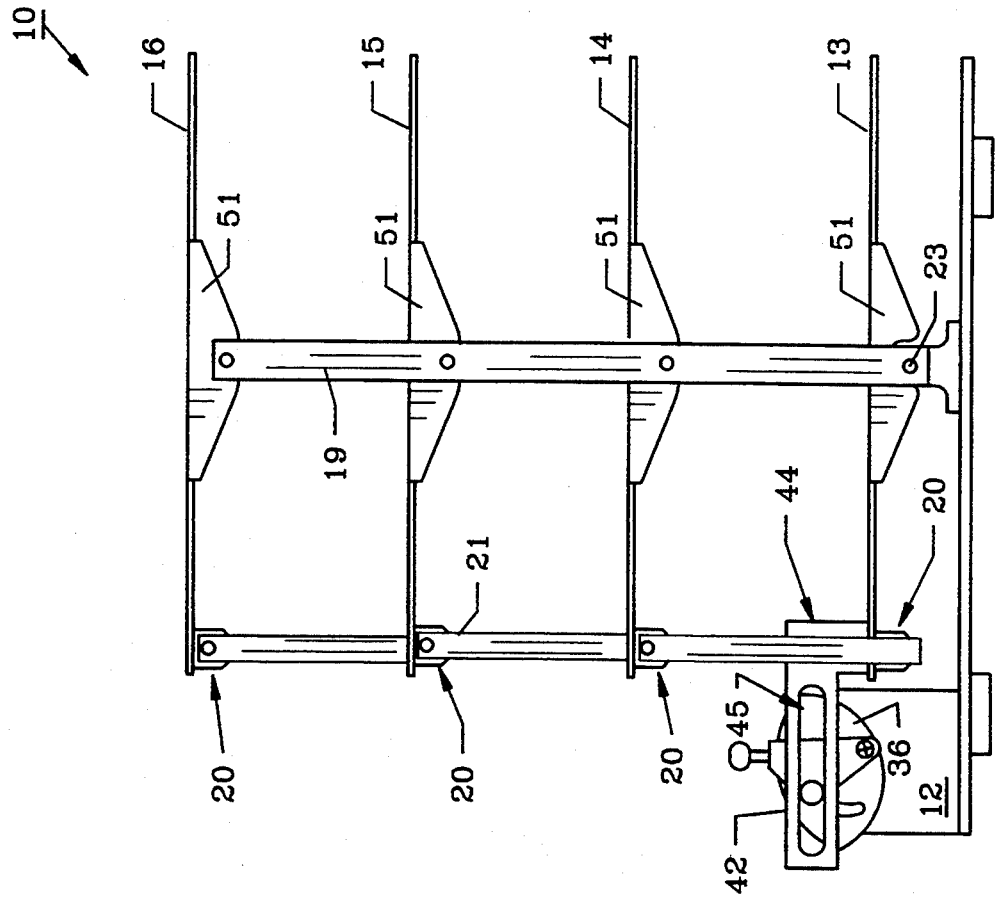
FIG. 3 illustrates a rear elevational view of the mixer as seen in FIGS. 1 and 2 but with the platforms horizontal.

Motor 17 comprises a fractional horsepower 24 v DC motor with an integral gear reduction or otherwise for operation at a relatively low rpm range. For example, motor 17 rotates at a maximum of 17 rpms and can be further slowed by motor control 24 as seen in FIG. 5. Motor control 24 is adjusted by control knob 25 which extends from the forward end 34 of motor housing 12. Motor housing 12 includes an elongated U-shaped top cover 26 as seen in FIGS. 2 and 3. Motor 17 is powered by 24 v DC received through supply cord 27. On/off switch 28 is also shown in FIG. 5 mounted on front 34 of housing 12. Fuses, connectors and the like are not shown in FIG. 5 as a complete electrical schematic is not illustrated but connections for the illustrated components would be understood by those skilled in the art. To remove motor housing 12 from base 11 screws 55 (FIG. 2) positioned within slots 29, 29' (FIG. 5) are loosened and motor housing 12 containing motor 17 is easily slid therefrom.. Key hole slot 30 found in the bottom of housing 12 receives screw 56 extending from the top of base 11 as would be understood and helps stabilize housing 12.

In operation, as motor 17 is turned on by switch 28, motor shaft 35 (FIG. 5) which is rigidly affixed to elliptically shaped cam 36 as shown in FIGS. 6, 7 and 8, revolves, driving cam 36. Cam 36 includes an arcuate cam slot 37 for adjusting the maximum to minimum tilt of platforms 13-16 as shown in FIGS. 1 and 2. Cam follower stud 38 rides within arcuate slot 37 and is adjustably positioned therealong by manually adjusting cam follower 39. As shown in FIG. 7, cam follower 39 pivots on cam 36 around cam follower pin 40 which secures cam follower 39 to cam 36 and passes through pin aperture 41 as shown in FIG. 8. Thumb screw 42 acts as a means to secure the desired pivotal position of cam follower 39 as it tightens against the outer edge of elliptically shaped cam 36 as shown in FIG. 9. Cam follower 39 comprises a substantially triangularly shaped thin stainless steel member which includes cam stud 43 which is axially aligned with cam follower stud 38 as seen in FIG. 9. Cam stud 43 slidably engages elongated cam connector slot 45 of cam connector 44 which is rigidly affixed to platform 13 as shown in FIG. 10 by welding or bolting. Cam stud 43 rotates within cam connector slot 45 as cam 36 turns to pivot or tilt platform 13 and other platforms which may be joined thereto. Thumb screw 42 can be loosened as desired and cam follower 39 moved upwardly as seen in FIG. 8 until it reaches its maximum height as shown with cam follower stud 38 seen in dotted lines. Thumb screw 42 is then tightened and platform 13 and other platforms 14-16 connected thereto by drive links 21 will pivot or tilt a maximum of only two degrees above and below the horizon. For greater agitation and mixing of containers placed on platforms 13-16, thumb screw 42 is loosened and cam follower stud 38 is urged downwardly along arcuate slot 37 to the bottom as seen in FIG. 8. When cam stud 38 reaches the lowest end of slot 37, platform 13 and any additional platforms linked thereto will pivot a maximum of approximately eleven degrees above and eleven degrees below the horizon. As would be understood, adjustments between the minimum two degrees and maximum eleven degrees can be set as desired.

As earlier explained, motor 17 drives cam 36 as motor shaft 35 is rigidly affixed within aperture 46 of cam 36. Thus, with the speed of motor 17 controllable and the tilt of platforms 13–16 adjustable, a wide variety of culture solutions, staining gels and other biological products can be agitated to precise standards.

Platforms 13–16 include front triangular shaped brace members 50 and rear braces 51 as shown in FIGS. 1 and 4. All such brace members have an aperture for receiving either axle rod 22 or axle stud 23 with the exception of bottom platform 13. Bottom platform 13 includes slot 52 in front brace 50 as shown in FIG. 10. Slot 52 allows quick assembly and also provides a safety feature in the event that an operator may inadvertently place his fingers beneath lower platform 13 while it is running. Slot 52 allows platform 13 to raise from axle rod 23 during tilting if necessary without injury to the operator's fingers placed beneath on base 11.

The illustrations and examples provided herein are for explanatory purposes and are not intended to limit the scope of the appended claims.

We claim:

1. A mixing device comprising: a base, a motor, said motor mounted on said base, a first rigid stanchion, said first stanchion fixed to said base, a first platform, said platform pivotally connected to said first stanchion, a cam connector, said cam connector attached to said platform, a cam, said cam defining an arcuate slot therein, said cam joined to said motor and to said cam connector, means to adjust said cam, said adjusting means attached to said cam whereby said motor will turn said cam and cause said first platform to pivot.

2. The mixing device of claim 1 and including a platform tab, said tab depending from said first platform.

3. The mixing device of claim 1 and including a plurality of platforms, said platforms pivotally joined to said first stanchion.

4. The mixing device of claim 1 and including a second platform said second platform rotatably joined to said first stanchion.

5. The mixing device of claim 1 and including a second platform, said second platform rotatably joined to said first stantion, and a second tab, said second tab depending from said second platform.

6. The mixing device of claim 5 and including a drive link, said drive link rotatably connected to said second tab.

7. The mixing device of claim 1 wherein said first platform includes a friction producing surface, said surface releasably attached to said platform.

8. The mixing device of claim 1 wherein said motor is sealed.

9. The mixing device of claim 1 wherein said motor extends above said first platform.

10. The mixing device of claim 1 and including a motor speed control, said speed control connected to said motor.

11. The mixing device of claim 10 wherein said speed control comprises a control knob.

12. A mixing device comprising: a base, a first stanchion, said stanchion rigidly affixed to said base, a lower platform, said lower platform pivotally connected to said stanchion, an upper platform, said upper platform in vertical alignment with said lower platform and pivotally connected to said stanchion, means to impart motion, and said motion imparting means joined to said lower platform.

13. The mixing device of claim 12 and including a drive link, said drive link connecting said upper platform to said lower platform.

14. The mixing device of claim 12 wherein said motion imparting means includes a motor, said motor extending above said lower platform.

15. The mixing device of claim 12 wherein said motion imparting means includes a cam, said cam defining an arcuate slot therein.

16. A mixing device comprising a base, a motor, said motor attached to said base, a first and a second stanchion, said first and said second stanchions rigidly fixed to said base, a first platform, said first platform pivotally connected to said first and to said second stanchions, a cam connector, the outer surface of said cam connector defining an elongated slot, said cam connector attached to said first platform, a cam, said cam having a substantially elliptical shape, the outer surface of said cam defining an arcuate slot, a cam follower, said cam follower pivotally mounted on said cam, cam follower securing means, said cam follower securing means threadably attached to said cam follower, a cam follower stud, said cam follower stud positioned in said arcuate slot, a cam stud, said cam stud extending from said cam follower and positioned in said elongated slot of said cam connector whereby rotation of said motor will turn said cam and pivot said platform.

17. The mixing device of claim 16 and including a second platform, said second platform pivotally connected to said first and said second stanchions, said second platform connected to said first platform.

18. The mixing device of claim 17 and including a drive link, said drive link connected to said first and said second platforms.

19. The mixing device of claim 16 and including a motor speed control, a speed control knob, said speed control knob connected to said speed control, and said speed control connected to said motor.

* * * * *